United States Patent [19]

Ingwersen et al.

[11] Patent Number: Plant 6,349

[45] Date of Patent: Oct. 25, 1988

[54] BOUGAINVILLEA TORCH GLOW

[76] Inventors: Jack D. Ingwersen, 1620 Ridgeway St., Oceanside, Calif. 92054; William M. Tomlinson, 6120 Paseo del Norte, Suite G-1, Carlsbad, Calif. 92008

[21] Appl. No.: 891,313

[22] Filed: Jul. 31, 1986

[51] Int. Cl.[4] ..... A01H 5/00

[52] U.S. Cl. ..... Plt./54

[58] Field of Search ..... Plt./54

*Primary Examiner*—Robert E. Bagwill

*Attorney, Agent, or Firm*—Francis X. LoJacono

[57] ABSTRACT

A bougainvillea Torch Glow plant which is defined by a unique torch-like floral arrangement formed along the substantially upright branching of the shrub that is compact in its branching and has dense foliage with the flowers being borne in dense oppositely branched cymes, which are axillary and are borne in the axils of almost all leaves from near the apex of the branch to from ten to forty centimeters down the branch, giving the appearance of a cylindrical spike, and wherein the roots are much thicker and more succulent than typical for bougainvillea.

1 Drawing Sheet

The present invention relates to a new and distinct variety of bougainvillea plant which was discovered by us as an apparent mutation amongst a group of bougainvillea plants of unknown parentage which were being grown by us in our cultivated commercial nursery gardens located in Oceanside, Calif.

Prior to our discovery aforementioned, we obtained from the Philippines a number of cuttings of various unidentified varieties of bougainvillea plants of unknown parentage from which we hoped to develop a stock of commercial plants suitable for propagation and sale in the United States. These original cuttings were in good condition at the time of planting in our Oceanside nursery, and thus we were successful in rooting the cuttings.

The exceptional plant aforementioned surprisingly was found to have a dense torch-like floral arrangement, and further differed from other bougainvillea varieties in its predominate upright and compact growth habit, its more succulent root system, and its unique cylindrical spike-like inflorescenses. Under closer observation of this unusual bougainvillea plant that developed from the original cuttings, it appeared to be quite different from all the other surrounding bougainvillea plants. Continued close observations of this unique plant and of progeny thereof asexually reproduced by us therefrom by means of cuttings, which we also planted in our gardens referred to in the foregoing, convinced us that they represent a new and distinct variety unlike any other formely known to us or previously reported or described in published literature, as evidenced by the combination of features which are outstanding in our new mutation.

In the following description of the plant, the color names and numbers used in describing the leaves, bracts and flowers are based on the nomenclature adopted by The British Horticultural Colour Charts, these being "Horticultural Chart I" and "Horticultural Chart II," issued by Wilson Colour Ltd., in collaboration with The Royal Horticultural Society. Chart I set shows "Copyright—Robert F. Wilson, 1938"; Chart II set shows "Copyright—Robert F. Wilson, 1941."

THE PLANT

Locality where grown and observed: Oceanside, Calif.

General characteristics: The plant is an upright branching shrub that is compact in its branching and has dense foliage.

Dimensions: The oldest plant seen in a shrub approximately two meters in height and approximately one meter in width.

Branches: Young branches are purplish green and minutely puberulent with extremely short upwardly curving hairs. Older branches are medium gray brown with the bark splitting lengthwise, revealing dark green inner layers. Branches are relatively slender and grow to a length of about one meter.

Roots: The roots are much thicker and more succulent than typical for bougainvillea.

Foliage:

*Amount.*—Very Dense.

*Size.*—Mature leaves vary from three to five centimeters in length and from two and one-half to three centimeters in width. The petiole is about one centimeter in length.

*Color.*—The upper surface of the leaves is approximately Spinach Green o960, but somewhat less gray; the lower surface is Spinach Green o960/2. The petiole is minutely puberulent with the same type of hairs found on the young branches.

*Shape.*—The leaves are ovate with the apex acuminate and the base rounded. The margin of the leaves is entire. The sides of the leaf curve upwards so that the leaf is concave upwards.

*Venation.*—The veins are very fine and widely spaced. The arrangement of the secondary veins is pinnate and alterate, although the basal pair of veins is subopposite. Higher order veins are extremely faint.

*Arrangement.*—Mature leaves are alternate in arrangement. Some young leaves are clustered in the axils of mature leaves, but most are produced singly near the apex of the branch.

*Texture.*—Leaves are moderately thick and somewhat fleshy.

Thorns: A thorn is produced in the axil of most leaves above the bud or branchlet, but are only well-developed on old branches. These thorns are stout, conical, and straight or somewhat down-curved, and may grow to a length of about one centimeter.

THE BLOOM

Arrangement: The flowers are borne in dense oppositely branched cymes that branch from two to three times. These cymes are axillary and are borne in the axils of almost all leaves from near the apex of the branch to ten to forty centimeters down the branch, giving the appearance of a cylindrical spike. The axes of the cymes are green or reddish.

Bracts: The bracts subtending the flowers are Peony Purple 729 or 729/1. They vary from two to two and one-half centimeters in length and from one and one-half to one and three-quarters centimeters in width. The overall shape is ovate with the apex broadly acute and the base rounded. The venation of the bracts is substantially like the venation of the leaves, but is somewhat more prominent.

Flowers:

*Arrangement.*—Each flower is subtended by a bract, and the pedicel is completely fused to the midrib of the bract. Each terminal axis of the inflorescence bears three flowers and their subtending bracts in a whorled arrangement.

*Calyx.*—The calyx is approximately Beetroot Purple 830. In cross-section the calyx tube is five-ribbed. The overall shape of the calyx is salverform, and the spreading limb and lobes are white. The calyx is approximately one and one-half centimeters in length, the tube two millimeters in diameter at its broadest point, and the spreading limb and lobes five millimeters in diameter. Externally the calyx is minutely puberulent with hairs like those on the young branches.

*Petals.*—These flowers have no petals.

*Stamens.*—Each flower has seven to ten stamens of unequal length enclosed within the calyx tube and therefore not visible in the intact flower. The anthers are yellow.

*Pistil.*—Each flower has a single pistil that is borne upon a short stipe. The style is lateral and bears an elongate brush-like stigma near its apex. All of these parts are enclosed in the calyx tube and not visible in the intact flower.

Fruits: No fruits or seeds are produced by the plant.

We claim:

1. A new and distinct variety of bougainvillea plant, substantially as herein shown and described, characterized particulary as to novelty by the unique torch-like floral arrangement formed along the substantially upright branching of the shrub that is compact in its branching and has dense foliage with the flowers being borne in dense oppositely branched cymes, which are axillary and are borne in the axils of almost all leaves from near the apex of the branch to ten to forty centimeters down the branch, giving the appearance of a cylindrical spike and including a highly succulent root system.

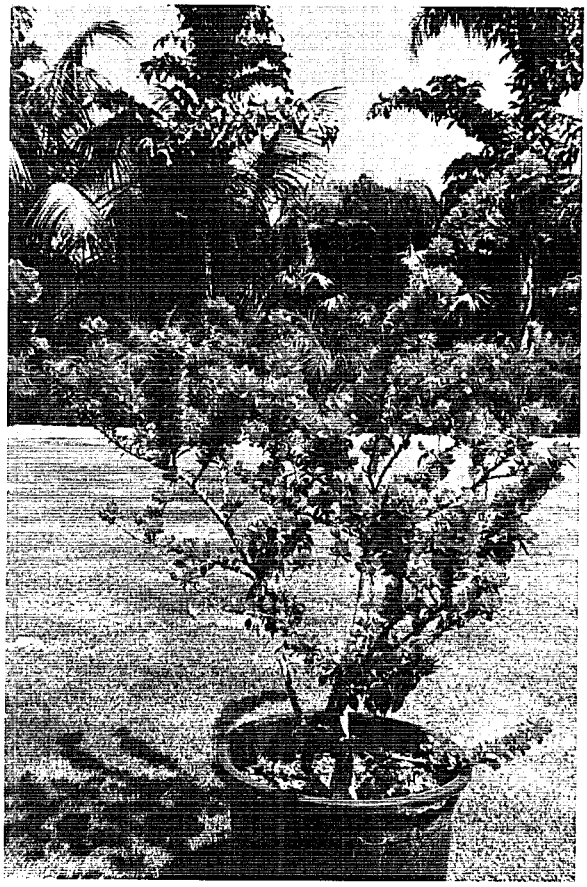
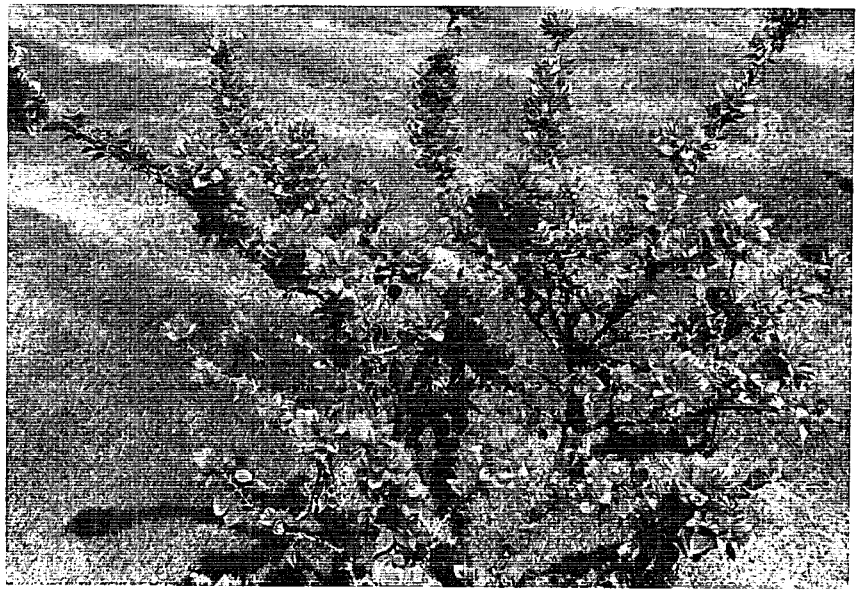

* * * * *